United States Patent
Wilson et al.

(10) Patent No.: US 12,308,852 B2
(45) Date of Patent: May 20, 2025

(54) CIRCUITRY FOR MEASUREMENT OF ELECTROCHEMICAL CELLS

(71) Applicant: Cirrus Logic International Semiconductor Ltd., Edinburgh (GB)

(72) Inventors: Paul Wilson, Linlithgow (GB); Ivan Perry, Penicuik (GB); John Priestley, Edinburgh (GB); James Wells, Edinburgh (GB)

(73) Assignee: Cirrus Logic Inc., Austin, TX (US)

( * ) Notice: Subject to any disclaimer, the term of this patent is extended or adjusted under 35 U.S.C. 154(b) by 211 days.

(21) Appl. No.: 18/192,257

(22) Filed: Mar. 29, 2023

(65) Prior Publication Data

US 2024/0305308 A1  Sep. 12, 2024

Related U.S. Application Data

(60) Provisional application No. 63/450,456, filed on Mar. 7, 2023.

(51) Int. Cl.
- *H03M 1/48* (2006.01)
- *H03M 1/10* (2006.01)
- *H03M 1/12* (2006.01)

(52) U.S. Cl.
CPC ......... *H03M 1/121* (2013.01); *H03M 1/1023* (2013.01)

(58) Field of Classification Search
CPC .... H03M 1/121; H03M 1/1023; H03M 1/124; A61B 5/14532; A61B 5/14546
See application file for complete search history.

(56) References Cited

U.S. PATENT DOCUMENTS

| | | | |
|---|---|---|---|
| 2022/0125352 A1* | 4/2022 | Varsavsky | A61B 5/14865 |
| 2023/0061184 A1 | 3/2023 | Lesso et al. | |

FOREIGN PATENT DOCUMENTS

DE    102018110575 A1    11/2018

OTHER PUBLICATIONS

Mamun et al: A Glucose Biosensor Using CMOS Potentiostat and Vertically Aligned Carbon Nanofibersr/IEEE Transactions On Biomedical Circuits and Systems, IEEE, US, vol. 10, No. 4, Aug. 1, 2016 (Aug. 1, 2016) pp. 807-816.

Invitation to Pay Additional Fees and, Where Applicable, Protest Fee, International Application No. PCT/GB2024/050592, Application No. PCT/GB2024/050592, mailed Jun. 26, 2024.

* cited by examiner

*Primary Examiner* — Jean B Jeanglaude
(74) *Attorney, Agent, or Firm* — Jackson Walker L.L.P.

(57) ABSTRACT

Circuitry for processing an analyte signal obtained from an electrochemical cell, the circuitry including: a first signal path between a first electrode of the electrochemical cell and a first input of an analog-to-digital converter (ADC) circuit, the first signal path comprising a first gain stage configured to convert the analyte signal to a first analog signal; a second signal path between the first electrode and a second input of the ADC circuit, the second signal path comprising a second gain stage configured to convert the analyte signal to a second analog signal; and switching circuitry configured to selectively couple the first electrode to the first input of the ADC circuit.

25 Claims, 7 Drawing Sheets

CIRCUITRY FOR MEASUREMENT OF ELECTROCHEMICAL CELLS

The present disclosure claims priority to U.S. Provisional Patent Application Ser. No. 63/450,456, filed Mar. 7, 2023, which is incorporated by reference herein in its entirety.

TECHNICAL FIELD

The present disclosure relates to circuitry for measuring characteristics in electrochemical sensors.

BACKGROUND

Electrochemical sensors are widely used for the detection of one or more particular chemical species, analytes, as an oxidation or reduction current. Such sensors comprise an electrochemical cell, consisting of two or more electrodes configured for contact with an analyte whose concentration is to be ascertained. Such sensors also comprise circuitry for driving one or more of the electrodes and for measuring a response at one or more of the electrodes.

Conventional measurement circuitry in electrochemical sensors may include a transimpedance amplifier or a current conveyor. Transimpedance amplifiers can be slow when operating at high frequencies. Current conveyors can suffer from accuracy issues due to lack of feedback in their output stages.

SUMMARY

According to a first aspect of the disclosure, there is provided circuitry for processing an analyte signal obtained from an electrochemical cell, the circuitry comprising: a first signal path between a first electrode of the electrochemical cell and a first input of an analog-to-digital converter (ADC) circuit, the first signal path comprising a first gain stage configured to convert the analyte signal to a first analog signal; a second signal path between the first electrode and a second input of the ADC circuit, the second signal path comprising a second gain stage configured to convert the analyte signal to a second analog signal; and switching circuitry configured to selectively couple the first electrode to the first input of the ADC circuit.

The second gain stage may have a higher accuracy than the first gain stage.

The first gain stage may have a higher output impedance than the second gain stage.

The second gain stage may comprise a transimpedance amplifier. The transimpedance amplifier may comprise: a feedback resistor coupled between the first electrode and the first input of the ADC circuit, wherein selectively coupling the first electrode to the first input of the ADC circuit comprises bypassing the feedback resistor.

Bypassing the feedback resistor may cause the gain stage to operate as a unity buffer between the first electrode and the first input of the ADC circuit.

The switching circuitry may be configured to switch circuitry between a first mode and a second mode. In the first mode, the circuitry may operate as a current conveyer. In the second mode, the circuitry may operate as a transimpedance amplifier (TIA).

The first gain stage may comprise a current conveyer.

The circuitry may further comprise the ADC circuit. The ADC circuit may comprise: a first ADC and a second ADC. The first ADC may be configured to convert the first analog signal to a first digital signal. The second ADC may be configured to convert the second analog signal to a second digital signal.

The first ADC may have a higher bandwidth than the second ADC.

The circuitry may further comprise a digital correction module configured to apply a correction factor to the first digital signal and output a corrected first digital signal. The correction factor may be configured to correct an error introduced by the first signal path.

The correction factor may be configured to correct one or more of: a DC offset in the first analog signal; a gain of the first analog signal; and distortion in the first analog signal.

The circuitry may further comprise memory for storing the correction factor.

The correction factor may be calculated based on a comparison between the first analog signal and the second analog signal.

During a calibration phase, the circuitry may be configured to: apply a calibration stimulus at the first electrode; measure the first analog signal responsive to the calibration stimulus; measured the second analog signal responsive to the calibration stimulus; and determining the correction factor based on the first and second analog signals.

The calibration stimulus may comprise one of: one or more DC signals; a swept DC signal; a combination of DC and AC signals (e.g., a chirp).

The circuitry may be configured to: monitor the analyte signal, the first analog signal and the second analog signal; and update the correction factor based on the monitored analyte signal, the first analog signal, and the second analog signal. The correction factor may be updated periodically or continuously.

According to another aspect of the disclosure, there is provided a system comprising: the circuitry of any one of the preceding claims; the electrochemical cell.

The electrochemical cell may comprise a counter electrode; the first electrode is a first working electrode of the electrochemical cell.

The electrochemical cell may comprise one or more second working electrodes.

The electrochemical cell may comprise an anode and a cathode. The first electrode may be the cathode.

According to another aspect of the disclosure, there is provided an analyte sensor comprising any of the circuitry or the systems described above.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of non-limiting examples with reference to the drawings, in which.

DESCRIPTION OF EMBODIMENTS

Figure 1:
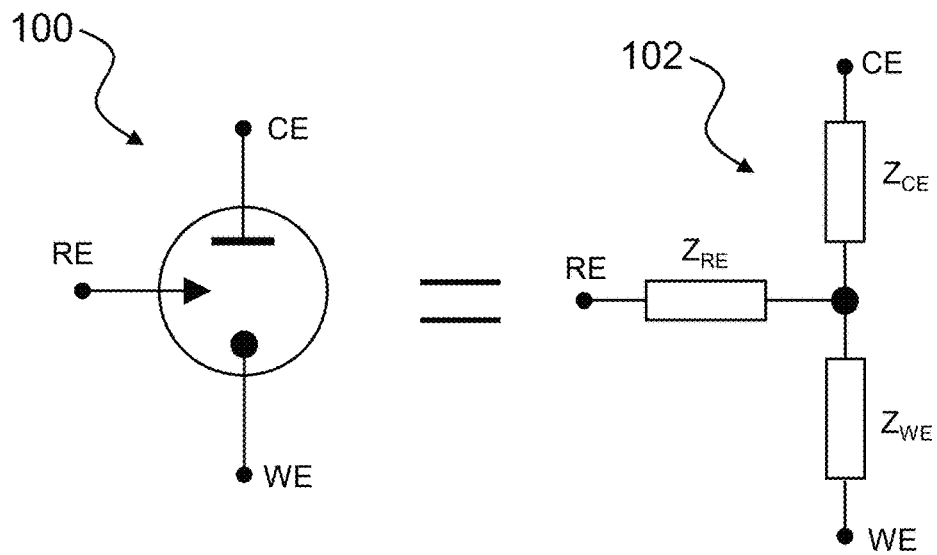
FIG. 1 illustrates a schematic diagram and electrical equivalent circuit for a three-electrode electrochemical cell.

FIG. 1 is a schematic diagram of an electrochemical cell 100 comprising three electrodes, namely a counter electrode CE, a working electrode WE and a reference electrode RE. FIG. 1 also shows an equivalent circuit 102 for the electrochemical cell comprising a counter electrode impedance ZCE, a working electrode impedance ZWE and a reference electrode impedance ZRE.

To determine a characteristic of the electrochemical cell, and therefore an analyte concentration, a bias voltage is applied at the counter electrode CE and a current at the working electrode WE is measured. Feedback is used to set the voltage VRE at the reference electrode RE to be equal to a bias voltage VBIAS1 (as is explained in more detail below) A current IWE at the working electrode WE is then measured. As the resistance in the cell 100 increases, the current measured at the working electrode WE decreases. Likewise, as the resistance in the cell 100 decreases, the current measured at the working electrode WE increases. Thus the electrochemical cell 100 reaches a state of equilibrium where the voltage drop between the reference electrode RE and the working electrode WE is maintained constant. Since the bias voltage at the counter electrode CE and the measured current at WE are known, a characteristic of the analyte contained in the cell 100 can be ascertained.

Figure 2:
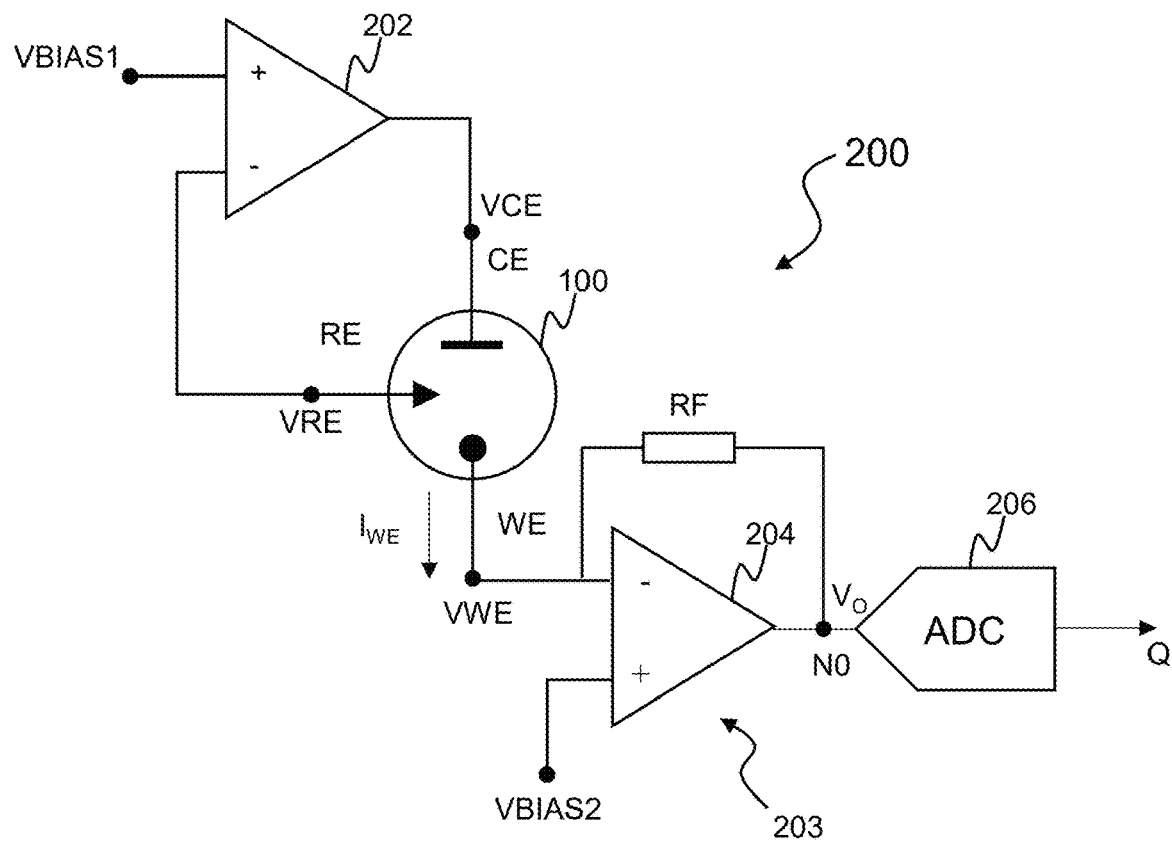
FIG. 2 is a schematic diagram of an example prior art measurement circuit.

FIG. 2 illustrates an example prior art drive and measurement circuit 200 which is configured to implement the above explained cell characterisation, specifically for measuring an analyte concentration in the electrochemical cell 100 shown in FIG. 1. The circuit 200 comprises a first amplifier 202 and a gain stage 203 comprising a second amplifier 204 and a feedback resistor RF. Each of the first and second amplifiers 202, 204 may comprise one or more op-amps. A non-inverting input of the first amplifier 202 is coupled to a bias voltage VBIAS1. An inverting input of the first amplifier 202 is coupled to the reference electrode RE. An output of the first amplifier 202 is coupled to the counter electrode CE and configured to drive the counter electrode CE with a counter electrode bias voltage VCE. The counter electrode bias voltage VCE applied at the counter electrode CE by the first amplifier 202 is proportional to the difference between the bias voltage VBIAS1 and the voltage VRE at the reference electrode RE. As such, the first amplifier 202 acts to maintain the voltage at the reference electrode RE at the bias voltage VBIAS1.

An inverting input of the second amplifier 204 is coupled to the working electrode WE and the non-inverting input of the second amplifier 204 is coupled to a reference voltage, VBIAS2. VBIAS2 may be set to a constant reference voltage, such as half the supply voltage of the circuit 200 (i.e., VDD/2). Alternatively, VBIAS2 may be variable. By controlling the bias voltage VBIAS1 and the reference voltage VBIAS2, a differential bias voltage between the working and reference electrodes WE, RE can be controlled.

A feedback loop comprising a feedback resistor RF is coupled between the inverting input and an output of the second amplifier 204. As such, the gain stage 203 operates as a transimpedance amplifier (TIA). The feedback serves to maintain the working electrode WE at the reference voltage VBIAS2 provided at the non-inverting input of the second amplifier 204. The gain stage 203 is thus operable to output an output voltage VO at an output node NO which is proportional to the current IWE at the working electrode WE. The output voltage VO is then provided to an analog-to-digital converter (ADC) 206 which outputs a digital output Q which represents the current IWE at the working electrode WE. As will be explained in more detail below, alternative gain arrangements to that shown in FIG. 2 exists for processing the working electrode current IWE. The arrangements shown in FIG. 2 is provided for example only.

To bias the counter electrode CE, and therefore the electrochemical cell 100, at different voltages, the bias voltage VBIAS1 may be adjusted, for example between ground (e.g. zero volts) and the supply voltage VDD. As an example, with the non-inverting input voltage VBIAS2 of the second amplifier 204 set at VDD/2, a positive bias may be applied to the cell 100 by maintaining the bias voltage VBIAS1 above VDD/2. Likewise, a negative bias may be applied to the cell 100 by maintaining the bias voltage VBIAS1 below VDD/2. Additionally or alternatively to varying the bias voltage VBIAS1, the reference voltage VBIAS2 may be adjusted to set the voltage at the working electrode WE, and therefore the electrochemical cell 100.

An advantage of the circuit 200 of FIG. 2 is its relative simplicity. Measurement is implemented using a single amplifier (the second amplifier 204) in combination with the feedback resistor RF. In addition, the use of feedback to set voltages at the counter, working and reference electrode CE, WE, RE of the electrochemical cell 100 minimises gain error through the signal path. This improves accuracy of the circuit 200, particularly for low bandwidth or near DC measurements, for example where changes in the working electrode current IWE are relatively slow. Such low bandwidth measurements may, for example, be in the region of 0.1 to 10 Hz, 0 to 10 Hz, or 0 to 1 Hz.

A disadvantage of the circuit 200 of FIG. 2 is that the working electrode WE of the electrochemical cell 100 is driven by the feedback resistor RF. Since the electrochemical cell 100 represents a complex capacitive load, this can have implications for frequency and/or magnitude of signals that can be driven across the cell 100. For example, driving a change in voltage at the working electrode WE at high frequencies may be slow when compared to driving such a change at low frequencies.

Figure 3:
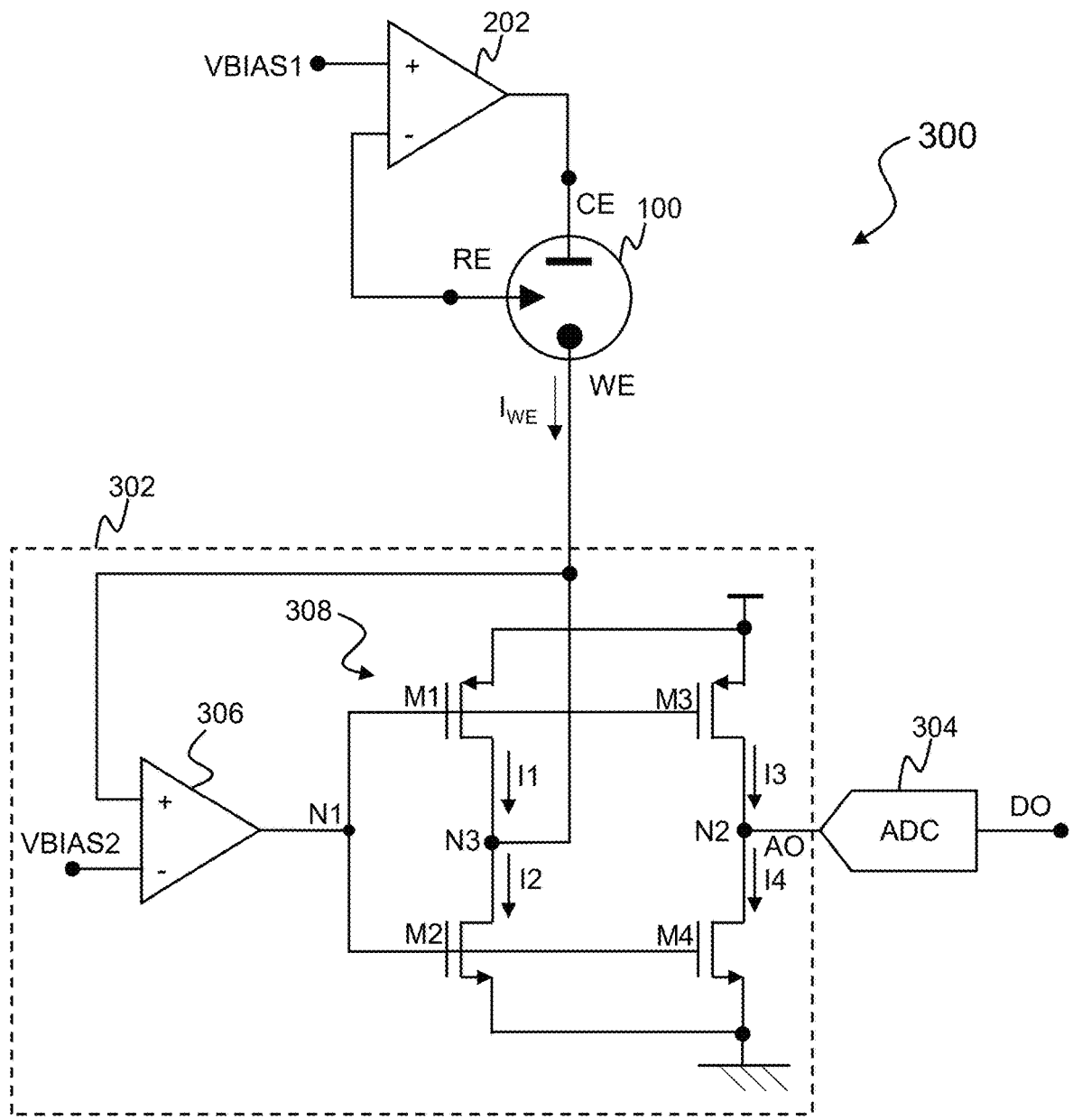
FIG. 3 is a schematic diagram of an example prior art measurement circuit.

FIG. 3 illustrates another example prior art drive and measurement circuit 300 which implements an alternative measurement regime to the drive and measurement circuit 200 shown in FIG. 2. Common parts of the circuits 200, 300 of FIGS. 2 and 3 denoted with common reference numerals.

Like the circuit 200, the circuit 300 comprises the first amplifier 202 having a non-inverting input coupled to a bias voltage VBIAS1 and an inverting input coupled to the reference electrode RE. The output of the first amplifier 202 is coupled to the counter electrode CE and configured to drive the counter electrode CE with a counter electrode bias voltage VCE. The counter electrode bias voltage VCE applied at the counter electrode CE by the first amplifier 202 is proportional to the difference between the bias voltage VBIAS1 and the voltage VRE at the reference electrode RE.

The circuit 300 further comprises a measurement circuit 302 and an ADC 304. The measurement circuit 302 is implemented as a current conveyor. In this example, the measurement circuitry 302 implements a second generation current conveyor (CCII) although other current conveyor topologies could be implemented without departing from the scope of the present disclosure. The measurement circuit 302 comprises a second amplifier 306 (e.g., an operational amplifier) and current mirror circuitry 308 comprising first, second, third and fourth transistors M1, M2, M3, M4. In this example, the transistors M1:M4 are MOSFETs. Specifically, the first and third transistors M1, M3 are PMOS devices and the second and fourth transistors M2, M4 are NMOS devices.

The second amplifier 306 comprises a non-inverting input coupled to the working electrode WE, an inverting input coupled to a reference voltage VBIAS2 and an output coupled to a first (intermediate) node N1.

Gates of each of the first, second, third and fourth transistors M1:M4 are coupled to the first node N1 and therefore the output of the second amplifier 306. Drains of the first and third transistor M1, M3 are coupled to a supply voltage VDD. Sources of the first and third transistors M1, M3 are coupled to drains of the second and fourth transistors M2, M4, respectively. Sources of the second and fourth transistors M2, M4 are coupled to a ground reference voltage (GND). The source of the third transistor M3 and the drain of the fourth transistor M4 are coupled at a second (output) node N2 to an input of the ADC 304. The source of the first transistor M1 and the drain of the second transistor M2 are coupled at a third (feedback) node N3 to the working electrode WE. As such, a feedback path is provided between the third node N3 and the non-inverting input of the second amplifier 306. The amplifier 306 is thus arranged as a unity gain amplifier or buffer amplifier. The first and second transistors M1, M2 operate as transconductors which generate first and second currents I1, I2 respectively. The working electrode current IWE is equal to the difference between the first and second currents (IWE=I2−I1). The first and second transistors M1, M2 act as input reference devices of a current mirror. The third and fourth transistors M3, M4 operate as output devices of the current mirror. The first current I1 is mirrored to a third current I3 generated by the third transistor N3. The second current I2 is mirrored to a fourth current I4 generated by the fourth transistor N4.

During operation, the working electrode current IWE is provided to the second amplifier 306 and this current IWE is amplified by unity and therefore buffered to the first node N1. During operation, the second amplifier 306 amplifiers the difference between the working electrode voltage VWE and the reference voltage VBIAS2. Combined with the negative feedback from the third node N3, the result is that the error voltage VWE-VBIAS2 becomes zero such that VBIAS2 and VWE become equal. Respective first and second currents I1, I2 are copied as respective third and fourth currents I3, I4 such that the analog output signal AO is a copy of the current IWE. The ADC 304 is thus configured as a current ADC (IADC) configured to output a digital output signal DO proportional to the current received from the second node N2.

The measurement circuit 302 of FIG. 3 has an advantage of ensuring low output impedance (when compared to the circuit 200) at each of the counter, reference and working electrodes CE, RE, CE, since the working electrode WE is driven directly by the first and second transistors M1, M2. Since the load across the electrochemical cell 100 is highly capacitive in nature, this inherent low output impedance may be advantageous when a stimulus of high amplitude and/or frequency is driven over the electrochemical cell 100.

A drawback of the circuit 300 of FIG. 3 is that any errors in gain between the current mirror input (comprising first and second transistors M1, M2) and the current mirror output (comprising third and fourth transistors M3, M4) can lead to errors in the analog output signal AO. Such errors may include one or more of DC offset error, non-linearity, gain error and additive noise. Such errors are exacerbated at low frequencies. As such, the measurement circuit 302 tends to operate more accurately at high bandwidths. Such high bandwidths may be at frequencies up to 100 kHz, or up to 200 kHz, or up to the megahertz range.

Embodiments of the present disclosure aim to address or at least ameliorate one or more of the drawbacks associated with each of the circuits 200, 300 shown in FIGS. 2 and 3. As noted above, advantages associated with the measurement circuit 302 (comprising the current conveyer) are most applicable in high bandwidth modes of operation, whereas the measurement circuit 200 (implementing the second amplifier 204 operating as a TIA) is better suited for operation at lower bandwidths. Embodiments of the disclosure implement a hybrid design in which a low bandwidth path comprises a feedback TIA that can be reconfigured into a unity gain amplifier whose output currents are mirrored through a current conveyor stage into a high bandwidth measurement ADC.

Figure 4:
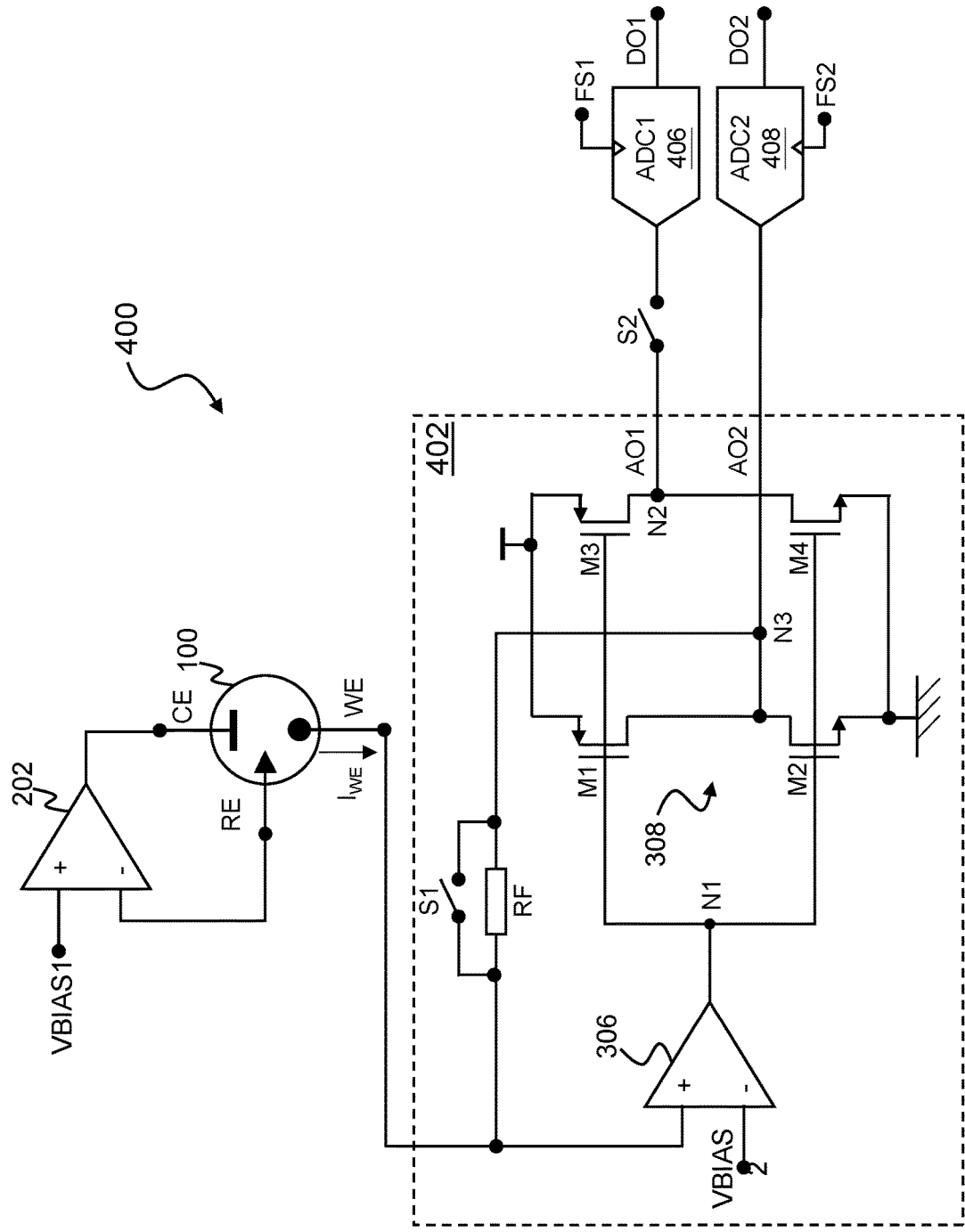
FIG. 4 is a schematic diagram of a measurement circuit for measuring characteristics of an electrochemical cell.

FIG. 4 illustrates an example drive and measurement circuit 400 according to embodiments of the present disclosure. Parts of the drive and measurement circuit 400 which are common to the circuits 200, 300 of FIGS. 2 and 3 have been given common reference numerals.

Like the circuits 200, 300, the circuit 400 comprises the first amplifier 202 having a non-inverting input coupled to a bias voltage VBIAS1 and an inverting input coupled to the reference electrode RE. The output of the first amplifier 202 is coupled to the counter electrode CE and configured to drive the counter electrode CE with a counter electrode bias voltage VCE. The counter electrode bias voltage VCE applied at the counter electrode CE by the first amplifier 202 is proportional to the difference between the bias voltage VBIAS1 and the voltage VRE at the reference electrode RE.

The drive and measurement circuit 400 further comprises a measurement circuit 402 and first and second ADCs 406, 408.

The measurement circuit 402 differs from the measurement circuit 306 shown in FIG. 3 in that a feedback resistor RF is provided in the feedback path between the third node N3 and the non-inverting input is the second amplifier 306. The feedback resistor RF is coupled between the third node N3 of the current conveyer circuitry 308 and the non-inverting input of the second amplifier 306 (and the working electrode WE of the electrochemical cell 100). In addition, a bypass switch S1 is provided in parallel with the feedback resistor RF.

The first ADC 406 has an input coupled to the second node N2. Thus, the first ADC 406 is configured to convert a first analog output signal AO1 at the second node N2 into a first digital output signal DO1. The first analog output signal AO1 is a copy of the working electrode current IWE. As such, the first ADC 406 is configured as a current ADC. Optionally, the input of the first ADC 406 may be selectively coupled to the second node N2 using a select switch S2. The first ADC 406 may be clocked by a first clock signal FS1.

The second ADC 408 has an input coupled to the third node N3. As such, the second ADC 408 is configured to convert a second analog output signal at the third node N3 into a second digital output signal which represents the signal output from the second amplifier 306. The second ADC 408 may be clocked by a second clock signal FS2.

By operating the bypass switch S1 (and optionally the select switch S2 if provided), the measurement circuit 402 may be configured in one of two modes.

In a first mode (a current conveyor mode), the bypass switch S1 (and optionally the select switch S2) may be controlled to be closed. This causes the feedback resistor RF to be bypassed by the bypass switch S1 such that the third node N3 is coupled directly to the non-inverting input of the second amplifier 306. Since no resistance is provided in the feedback path of the second amplifier 306, the second amplifier 306 operates as a unity gain buffer. As such, when the bypass switch S1 is closed, the measurement circuit 402 operates as a current conveyor, mirroring the working electrode current IWE at the second node N2 which is coupled to input of the first (current) ADC 406 (optionally via the closed select switch S2 if provided).

In a second mode (a TIA mode), the bypass switch S1 (and optionally the select switch S2) is controlled to be open. This causes the feedback resistor RF to provide resistance in the feedback path between the output and the non-inverting input of the second amplifier 306, via the first and second transistors M1, M2. The second amplifier 306 therefore operates as a TIA converting the working electrode current IWE to a voltage (analog output signal AO2) at the third node N3. This analog output signal (voltage) AO2 is provided to the second ADC 408 which is configured as a voltage input ADC. It will be appreciated that the current output signal AO1 will still be generated in this second mode. As such, this current output signal AO1 may be used in addition to the voltage output signal AO2. Optionally, therefore, the first and second ADCs 406, 408 may therefore be operable to receive respective first and second output signal AO1, AO2 simultaneously.

It will be appreciated that since the first ADC 406 is configured to receive the first analog output signal AO1 from the second node N2 of the current conveyor 308, the first ADC 406 may be configured as a current input ADC. In an alternative embodiment, the first ADC 406 may be configured as a voltage input ADC with a TIA (not shown) provided at its input to convert the current at the second node N2 to a voltage to be provided to the first ADC 406.

It will also be appreciated that since the second ADC 406 is configured to receive the second analog output signal AO2 from the third node N3 (i.e. the output stage of the second amplifier 306 operating as a TIA), the second ADC 408 may be configured as a voltage input ADC. Alternatively, the second ADC 406 may be configured as a current ADC with a transconductance amplifier (not shown) provided at its input to convert the voltage at the third node N3 to a current in to be provided to the second ADC 408.

It will be appreciated that in the second (TIA) mode, the measurement circuit 402 may more accurately process signals at low frequency when compared to the operation in the first (current conveyor) mode. In contrast, in the first (CC) mode, the measurement circuit 402 may process higher frequency signals more efficiently and/or accurately. As such, the first ADC 406 may be configured to convert signals at higher bandwidths than the second ADC 408. For example, the first clock signal FS1 used to clock the first ADC 406 may have a higher frequency than the second clock signal FS2 used to clock the second ADC 408.

In the embodiment shown in FIG. 4, the first and second ADCs 406, 408 are provided. In other embodiments, the first and second ADCs 406, 408 may be replaced with a single ADC, for example as shown in FIG. 5.

Figure 5:
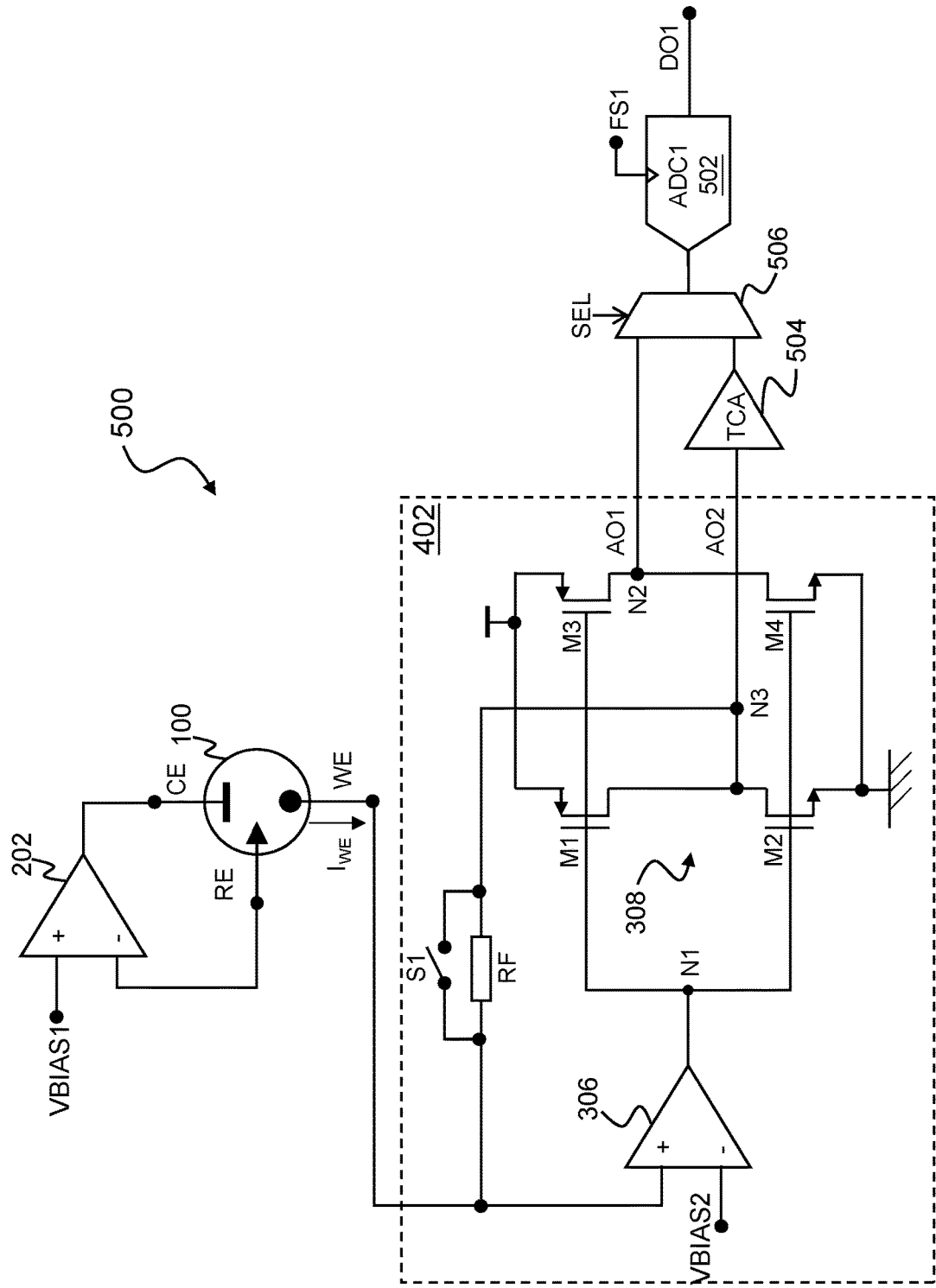
FIG. 5 is a schematic diagram of a measurement circuit which is a variation of the circuit shown in FIG. 4.

FIG. 5 illustrates a drive and measurement circuit 500 which is a variation of the circuit 400 shown in FIG. 4, like parts having been given like numbering. The first and second ADCs 406, 408 and the select switch S2 of the circuit 400 of FIG. 4 have been replaced with an ADC 502, a transconductance amplifier (TCA) 504 and a multiplexer 506. The second node N2 is coupled to a first input of the multiplexer 506. The third node N3 is coupled to an input of the TCA 504 which converts the second analog output signal AO2 from a current to an output voltage at the TCA 504's output. The output of the TCA 504 is coupled to a second input to the multiplexer 506. An output of the multiplexer is coupled to an input of the ADC 502. The multiplexer 506 is thus configured to selectively couple one of its first and second inputs to the ADC 502 based on a select signal SEL. The ADC 502 in this embodiments is thus implemented as a current input ADC. The multiplexer 506 may be configured to switch between the first and second analog output signal paths AO1, AO2 in alignment with switching of the bypass switch S1. For example, the select signal SEL may be switched to select the first analog output AO1 when the bypass switch S1 is closed and to select the second analog output AO2 when the bypass switch S1 is open.

In a variation of the above, instead of the TCA 504 being provided between the third node N3 and the second input of the multiplexer 506, a TIA may be provided between the second node N2 and the first input of the multiplexer 506 to convert a current at the second node N2 to a voltage to be provided to the ADC 502. In which case, the ADC 502 may be implemented as a voltage input ADC.

The hybrid solutions proposed above with reference to FIGS. 4 and 5 provides several advantages. For example, in the first mode, in which the measurement circuit 402 is operated as a current conveyor, the output impedance at the working electrode is minimized, which may be preferable for high frequency measurements. In addition, in the second mode, the TIA allows for high accuracy measurement due to the use of feedback (via the feedback resistor). Further, in both of the first and second modes, feedback can be used to set voltages at each of the counter, reference and working electrodes CE, RE, WE of the cell 100.

The hybrid architecture shown can additionally be implemented with few additional circuit elements when compared with the standard TIA architecture shown in FIG. 1. Referring to FIG. 4, the measurement circuit 402 may be implemented with the addition of a single switch S1 to configure the second amplifier 306 as a unity gain buffer, and a current mirror (comprising the third and fourth transistors M3, M4) provided in parallel to the first and second transistors M1, M2 to serve as the output stage for the current conveyor in the first mode.

It will be appreciated that when the measurement circuit 402 is operated in the first (CC) mode, the accuracy of measurement of the properties of the cell 100 may be affected. This is due in part to the fact that the current mirror comprising the third and fourth transistors M3, M4 does not form part of the feedback path between the output and non-inverting input of the second amplifier 306. Operation of the measurement circuit 402 in this first (CC) mode can therefore lead to the addition of DC offset, gain error, distortion and/or noise.

To mitigate the effect of offset, gain error, distortion and/or noise during operation of the measurement circuit 402 in the first mode, digital correction may be implemented at the output of the first ADC 406 to correct error in the first digital output signal DO1.

Figure 6:
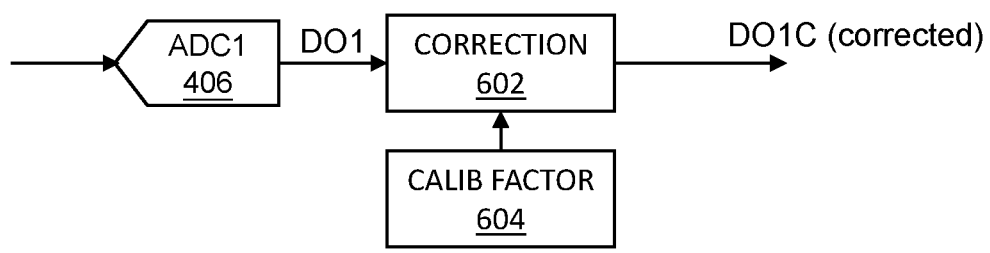
FIG. 6 is a block diagram of a correction module for correcting a digital output signal generated by the measurement circuit of FIG. 4.

FIG. 6 illustrates an example implementation of correction of the first digital output signal DO1. The first digital output signal DO1 may be provided to a correction module 602 configured to correct the first digital output signal DO1 and output a corrected digital output signal DO1C. The correction module 602 may correct the first digital output signal DO1 based on a calibration factor 604 which may be stored in memory (remote or local to the circuit 400). The calibration factor 604 may account for one or more effects associated with operation of the measurement circuit 402 in the second (CC) mode, including but not limited to one or more of DC offset, gain error, distortion and/or noise.

The calibration factor 604 may be obtained during a calibration process. Such a calibration proves may be performed during production and/or testing of the measurement circuit 402.

When the measurement circuit 402 is operated in the first (TIA) mode, the third and fourth transistors M3, M4 are not used to generate the first digital output signal DO1. Instead, the first and second transistors M1, M2, which are in the feedback loop of the second amplifier 306, are used to generate the first digital output signal DO1. Because of this, the first digital output signal DO1 (or the first analog output signal AO1) can be used as a reference in the calibration process.

Referring, for example, to FIG. 4, the circuit 400 may be stimulated with appropriate input stimuli. Such stimuli may be applied, for example, at the working electrode WE. The input stimuli may comprise of DC signals (constant and/or swept) or some combination of DC and AC signals. Such input stimuli may be applied to the circuit 400 during the calibration process.

The first and second digital output signal DO1, DO2 may be compared to determine an error in the first digital output signal DO1 at various input signal conditions (thereby using the second digital output signal DO2 as a reference). Such errors can then be used to generate the calibration factor 604 which may be frequency and time dependent.

Additionally or alternatively, a calibration process may use a signal at the working electrode WE during normal operation of the circuit 400. Realtime comparison of the first and second digital output signals DO1, DO2 may be used to continuously correct for errors in the first digital output signal substantially continuously or periodically to ensure that the corrected first digital output signal remains accurate during operation of the measurement circuit 402.

Embodiments above are described with reference to a three-electrode cell 100 comprising a counter electrode CE, a working electrode WE and a reference electrode RE. Embodiments of the disclosure are not, however, limited to having three-electrodes. The concepts described herein are equally applicable to two-electrode cells. In particular, in any of the embodiments described above, the three-electrode cell 100 may be replaced with a two-electrode cell.

Figure 7:
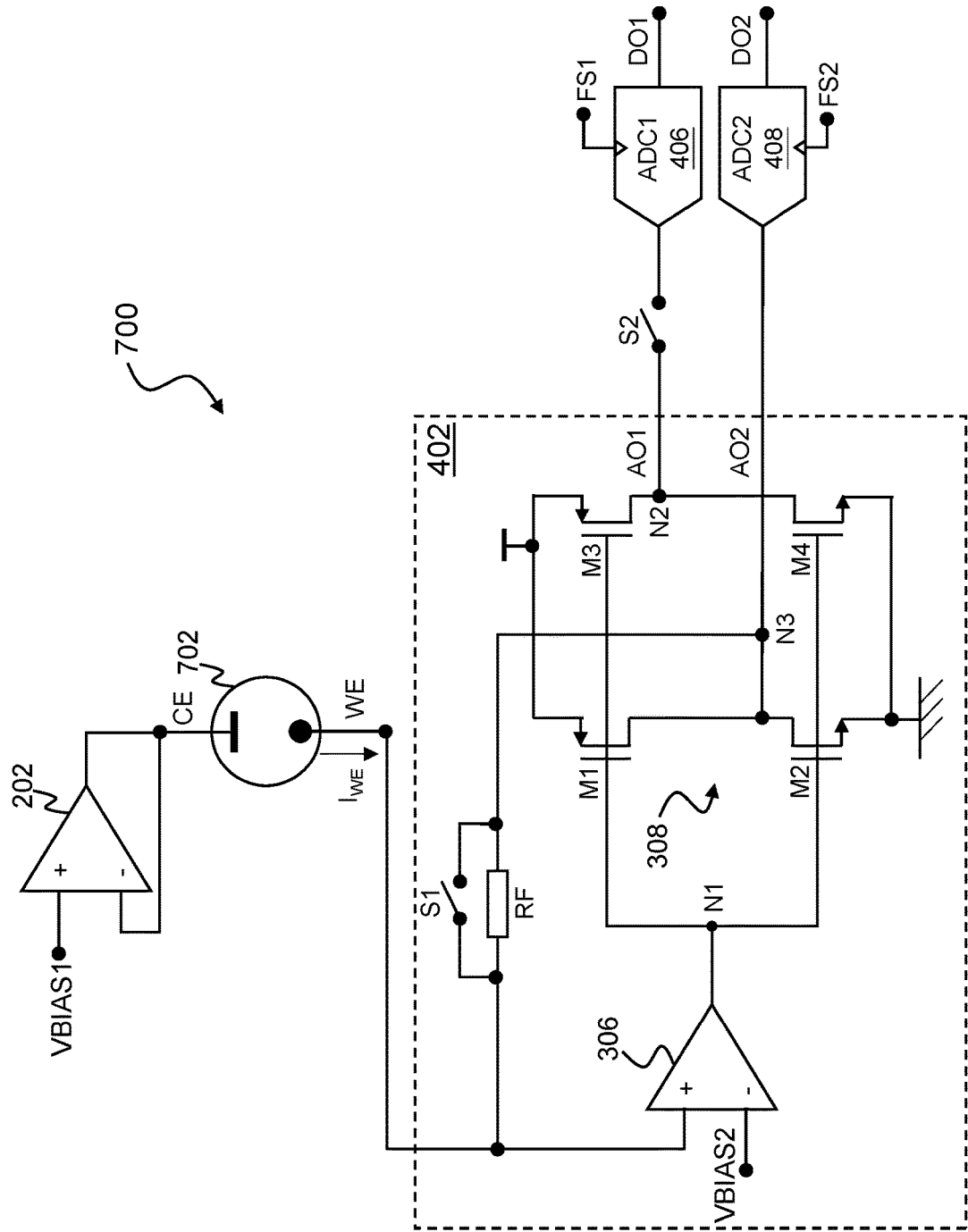
FIG. 7 is a schematic diagram of a measurement circuit for measuring characteristics of a two-electrode electrochemical cell.

FIG. 7 is an example drive and measurement circuit 700 which is a variation of the circuit 400 shown in FIG. 4, like parts having been given like numbering. In the circuit 700, the cell 100 has been replaced with a two-electrode cell 702. The counter electrode CE of the cell 702 is coupled to the output of the first amplifier 202. The working electrode WE of the cell 702 is coupled to the non-inverting input of the second amplifier 306. The inverting input of the first amplifier 202 is coupled to the counter electrode CE of the cell 702. This is in contrast to the arrangement in FIG. 4 in which the inverting input of the first amplifier 202 is coupled to the reference electrode RE of the cell 100.

Embodiments are described above with reference to cells 100, 702 comprising a single counter electrode CE and a single working electrode WE. Embodiments of the disclosure are not, however, limited to having cells having only one counter electrode or only one working electrode. The concepts described herein are equally applicable to cells comprising multiple working electrodes or multiple counter electrodes. In doing so, such sensors may either providing redundancy or enabling the sensing of multiple analytes in a single chip. This may be particularly advantageous in applications such as continuous glucose monitoring, where it may be desirable to measure concentrations of several analytes including but not limited to two or more of glucose, ketones, oxygen, lactate, and the like.

Figure 8:
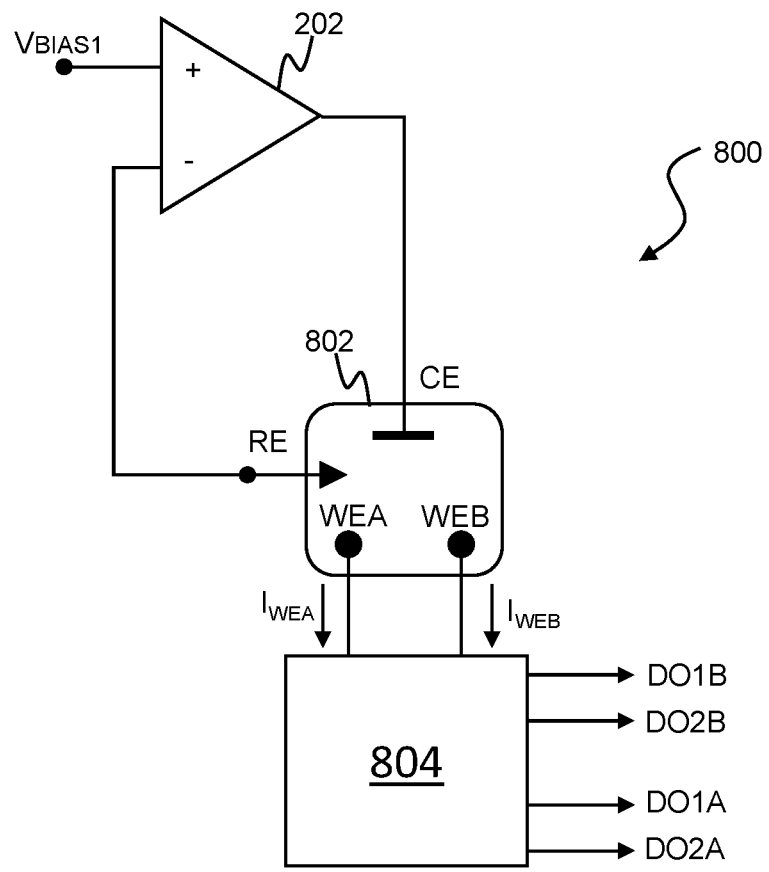
FIG. 8 is a schematic diagram of a measurement circuit for measuring characteristics of an electrochemical cell comprising two working electrode.

FIG. 8 illustrates an example drive and measurement circuit 800. Where like parts have been given like numbering. In the circuit 800, an electrochemical cell 802 comprising first and second working electrode WEA, WEB, a counter electrode CE and a reference electrode RE. A measurement circuit 804 is provided which outputs first and second digital output signals DO1A, DO2B based on a current $I_{WEA}$ derived from the first working electrode WEA and outputs first and second digital output signals DO1B, DO2B based on a current $I_{WEB}$ derived from the second working electrode WEB. The measurement circuit 804 may, for example, comprise two processing channels, each processing channel implementing the circuitry shown in FIG. 4 or 5. Alternatively, the measurement circuit may be implemented using a single processing stream multiplexed by a multiplexer (not shown). In either case, the measurement circuit 804 may be operable to hold the first and second working electrodes WEA, WEB at different voltages. This may be particularly useful when measuring different analytes with the first and second working electrodes WEA, WEB.

It will be appreciated that, whilst the embodiment described comprises two working electrodes WEA, WEB, in other embodiments three or more counter electrodes may be provided.

In the embodiments described herein, the electrochemical cells 100, 502 have been described in the form of an electrochemical sensor comprising counter and working electrodes CE, WE. For such sensors, the stimulus is typically a voltage, and the measured response is a current. It will be appreciated that embodiments of the present disclosure are not limited to such cells and extend to other types of cells, such as electrochemical cells acting as a power source (i.e. a battery). For batteries and the like, the driving stimulus of the cell is typically a current, and the measured response a voltage.

The various circuitry and electrochemical cells described herein may be incorporated into a continuous analyte sensor or a continuous glucose sensor or a continuous glucose monitor. The terms "continuous analyte sensor", "continuous glucose sensor", and "continuous glucose monitor" as used herein, will be well-known to a person of ordinary skill in the art and are not to be limited to a special or customized meaning. These terms refer, without limitation, to a device that continuously measures a concentration of an analyte/glucose and/or calibrates the sensor or an electrochemical cell incorporated therein (e.g., by continuously adjusting or determining the sensor's sensitivity and background).

The skilled person will recognise that some aspects of the above-described apparatus and methods may be embodied as processor control code, for example on a non-volatile carrier medium such as a disk, CD- or DVD-ROM, programmed memory such as read only memory (Firmware), or on a data carrier such as an optical or electrical signal carrier. For many applications embodiments of the invention will be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog™ or VHDL (Very high speed integrated circuit Hardware Description Language). As the skilled person will appreciate, the code may be distributed between a plurality of coupled components in communication with one another. Where appropriate, the embodiments may also be implemented using code running on a field-(re)programmable analogue array or similar device in order to configure analogue hardware.

Note that as used herein the term module shall be used to refer to a functional unit or block which may be implemented at least partly by dedicated hardware components such as custom defined circuitry and/or at least partly be implemented by one or more software processors or appropriate code running on a suitable general purpose processor or the like. A module may itself comprise other modules or functional units. A module may be provided by multiple components or sub-modules which need not be co-located and could be provided on different integrated circuits and/or running on different processors.

Embodiments may be implemented in a host device, especially a portable and/or battery powered host device such as a mobile computing device for example a laptop or tablet computer, a games console, a remote control device, a home automation controller or a domestic appliance including a domestic temperature or lighting control system, a toy, a machine such as a robot, an audio player, a video player, or a mobile telephone for example a smartphone. Embodiments may be implemented in a wearable or implanted host device, such as a continuous glucose monitor or the like.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope.

The invention claimed is:

1. A circuitry for processing an analyte signal obtained from an electrochemical cell, the circuitry comprising:
   a first signal path between a first electrode of the electrochemical cell and a first input of an analog-to-digital converter (ADC) circuit, the first signal path comprising a first gain stage configured to convert the analyte signal to a first analog signal;
   a second signal path between the first electrode and a second input of the ADC circuit, the second signal path comprising a second gain stage configured to convert the analyte signal to a second analog signal; and
   switching circuitry configured to selectively couple the first electrode to the first input of the ADC circuit.

2. The circuitry of claim 1, wherein the second gain stage has a higher accuracy than the first gain stage.

3. The circuitry of claim 1, wherein the first gain stage has a higher output impedance than the second gain stage.

4. The circuitry of claim 1, wherein the second gain stage comprises a transimpedance amplifier.

5. The circuitry of claim 4, wherein the transimpedance amplifier comprises:
   a feedback resistor coupled between the first electrode and the first input of the ADC circuit, wherein selectively coupling the first electrode to the first input of the ADC circuit comprises bypassing the feedback resistor.

6. The circuitry of claim 5, wherein bypassing the feedback resistor causes the gain stage to operate as a unity buffer between the first electrode and the first input of the ADC circuit.

7. The circuitry of claim 1, wherein the switching circuitry is configured to switch circuitry between a first mode and a second mode, wherein:
in the first mode, the circuitry operates as a current conveyer; and
in the second mode, the circuitry operates as a transimpedance amplifier (TIA).

8. The circuitry of claim 1, wherein the first gain stage comprises a current conveyer.

9. The circuitry of claim 1, further comprising:
the ADC circuit.

10. The circuitry of claim 9, wherein the ADC circuit comprises:
a first ADC, the first ADC configured to convert the first analog signal to a first digital signal; and
a second ADC, the second ADC configured to convert the second analog signal to a second digital signal.

11. The circuitry of claim 10, wherein the first ADC has a higher bandwidth than the second ADC.

12. The circuitry of claim 10, further comprising:
a digital correction module configured to apply a correction factor to the first digital signal and output a corrected first digital signal, the correction factor configured to correct an error introduced by the first signal path.

13. The circuitry of claim 12, wherein the correction factor is configured to correct one or more of:
a DC offset in the first analog signal;
a gain of the first analog signal; and
distortion in the first analog signal.

14. The circuitry of claim 12, further comprising memory for storing the correction factor.

15. The circuitry of claim 12, wherein the correction factor is calculated based on a comparison between the first analog signal and the second analog signal.

16. The circuitry of claim 12, wherein during a calibration phase, the circuitry is configured to:
apply a calibration stimulus at the first electrode;
measure the first analog signal responsive to the calibration stimulus;
measured the second analog signal responsive to the calibration stimulus; and
determining the correction factor based on the first and second analog signals.

17. The circuitry of claim 16, wherein the calibration stimulus comprises one of:
one or more DC signals;
a swept DC signal;
a combination of DC and AC signals.

18. The circuitry of claim 12, wherein the circuitry is configured to:
monitor the analyte signal, the first analog signal and the second analog signal; and
update the correction factor based on the monitored analyte signal, the first analog signal, and the second analog signal.

19. The circuitry of claim 18, wherein the correction factor is updated periodically or continuously.

20. A system comprising:
the circuitry of claim 1;
the electrochemical cell.

21. The system of claim 20, wherein:
the electrochemical cell comprises a counter electrode;
the first electrode is a first working electrode of the electrochemical cell.

22. The system of claim 21, wherein the electrochemical cell comprises one or more second working electrodes.

23. The system of claim 21, wherein the electrochemical cell comprises an anode and a cathode, wherein the first electrode is the cathode.

24. An analyte sensor comprising the system of claim 20.

25. An analyte sensor comprising the circuitry of claim 1.

* * * * *